(12) United States Patent
Gamble

(10) Patent No.: US 6,959,615 B2
(45) Date of Patent: Nov. 1, 2005

(54) SAMPLE COLLECTION AND PROCESSING DEVICE

(76) Inventor: Kimberly R. Gamble, 5690 The 12th Fairway, Suwanee, GA (US) 30024

(*) Notice: Subject to any disclaimer, the term of this patent is extended or adjusted under 35 U.S.C. 154(b) by 6 days.

(21) Appl. No.: 10/680,599

(22) Filed: Oct. 7, 2003

(65) Prior Publication Data

US 2004/0069076 A1 Apr. 15, 2004

Related U.S. Application Data

(63) Continuation-in-part of application No. 09/620,331, filed on Jul. 20, 2000, which is a continuation-in-part of application No. 09/263,229, filed on Mar. 5, 1999, now abandoned.

(51) Int. Cl.[7] .............................................. G01N 1/00
(52) U.S. Cl. .............................. 73/863.71; 73/864.14; 73/864.24; 422/103; 436/47
(58) Field of Search ...................... 73/864.24, 864.14, 73/863.71, 864.86, 864.87, 863.85, 864.74; 422/100, 101, 103; 436/180, 47

(56) References Cited

U.S. PATENT DOCUMENTS

| | | | |
|---|---|---|---|
| 3,991,627 A * | 11/1976 | Laird et al. ............... | 73/864.16 |
| 4,585,435 A * | 4/1986 | Vaillancourt ............... | 604/518 |
| 4,713,974 A * | 12/1987 | Stone ....................... | 73/864.23 |
| 4,935,010 A | 6/1990 | Cox et al. | |
| 5,407,269 A * | 4/1995 | Sherry et al. ............ | 366/174.1 |
| 5,567,309 A | 10/1996 | Classon et al. | |
| 5,945,070 A | 8/1999 | Kath et al. | |
| 6,526,812 B2 * | 3/2003 | Martin et al. ............ | 73/864.81 |
| 2002/0168778 A1 * | 11/2002 | Andrien et al. ............ | 422/100 |

* cited by examiner

Primary Examiner—Hezron Williams
Assistant Examiner—Nashmiya Fayyaz
(74) Attorney, Agent, or Firm—Kenneth S. Watkins, Jr.

(57) ABSTRACT

A sample processing device [700] comprises an elongated body [101] with a septum seal [109] on one end and a drip tube [731] on the second end. A small-diameter through-chamber [103] in the body provides a receiving and alignment chamber for a hypodermic needle [109] inserted into the septum. A sample processing chamber [709] provides a location for processing elements such as filters and adsorption or absorption frits [135,137]. Sample fluid injected into, or withdrawn from, the device by the hypodermic needle communicates with a bottom opening [701] of the drip tube via a drip tube nozzle [705], the sample processing chamber and the small-diameter chamber. The device is particularly useful in automated testing where the device is moved to various processing locations by the hypodermic needle.

18 Claims, 8 Drawing Sheets

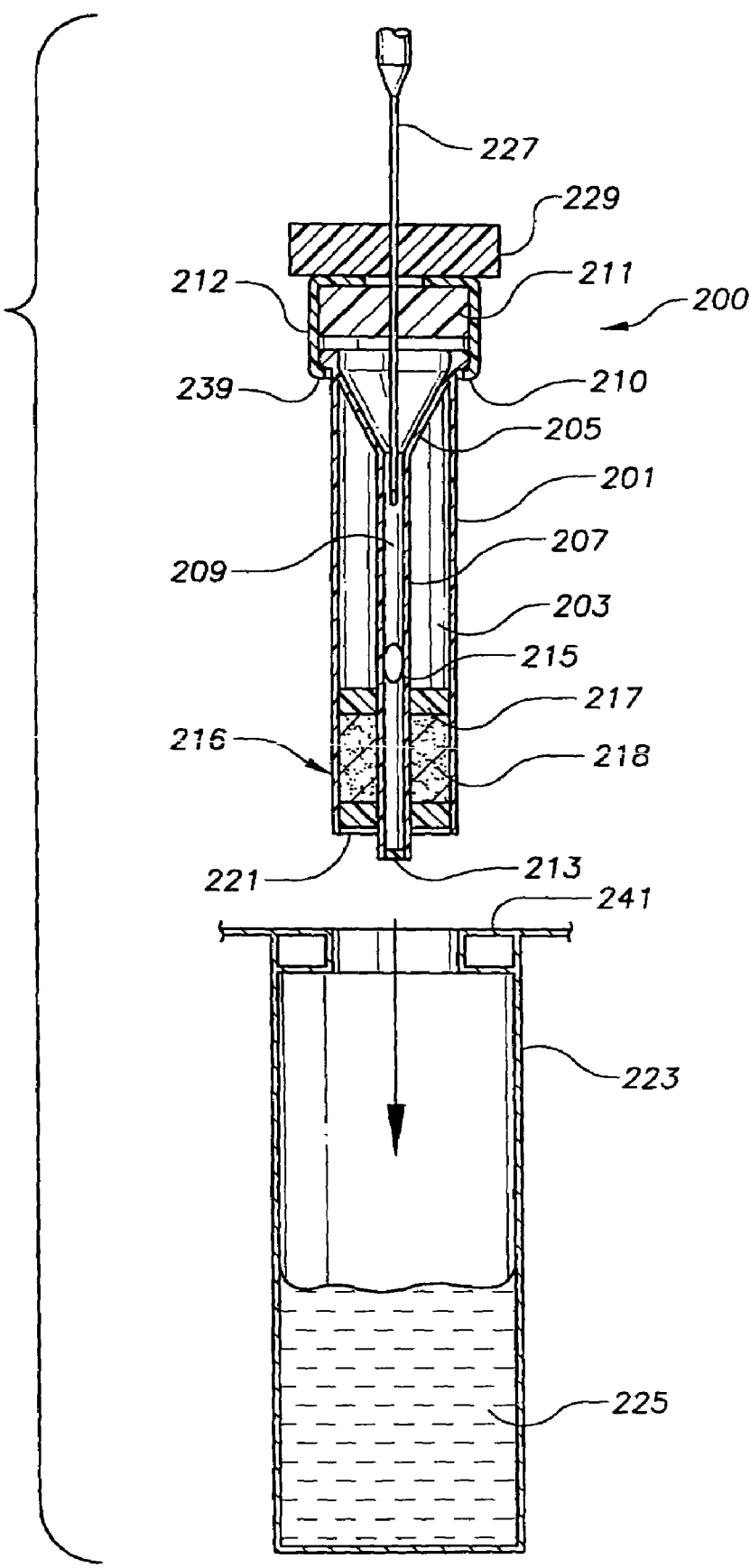

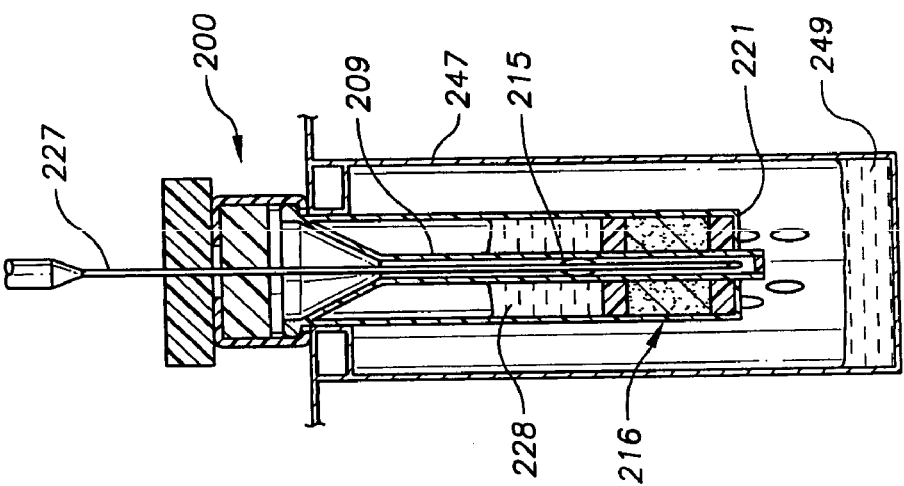
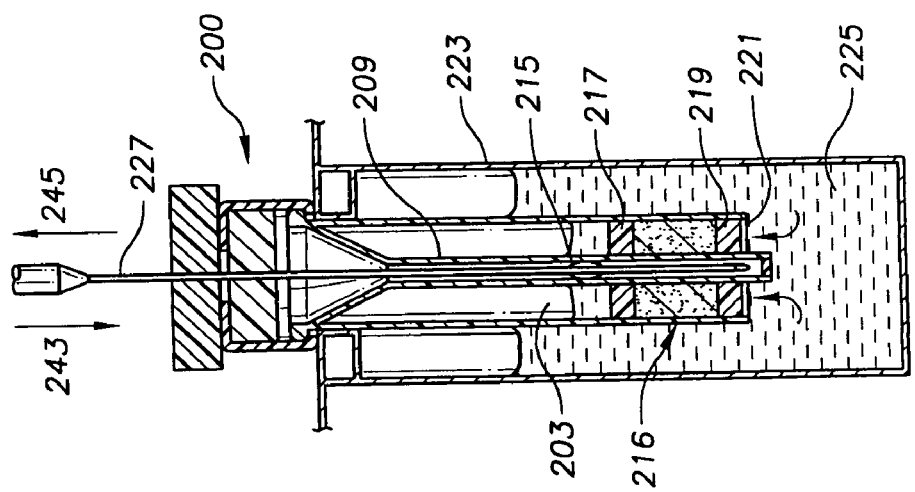

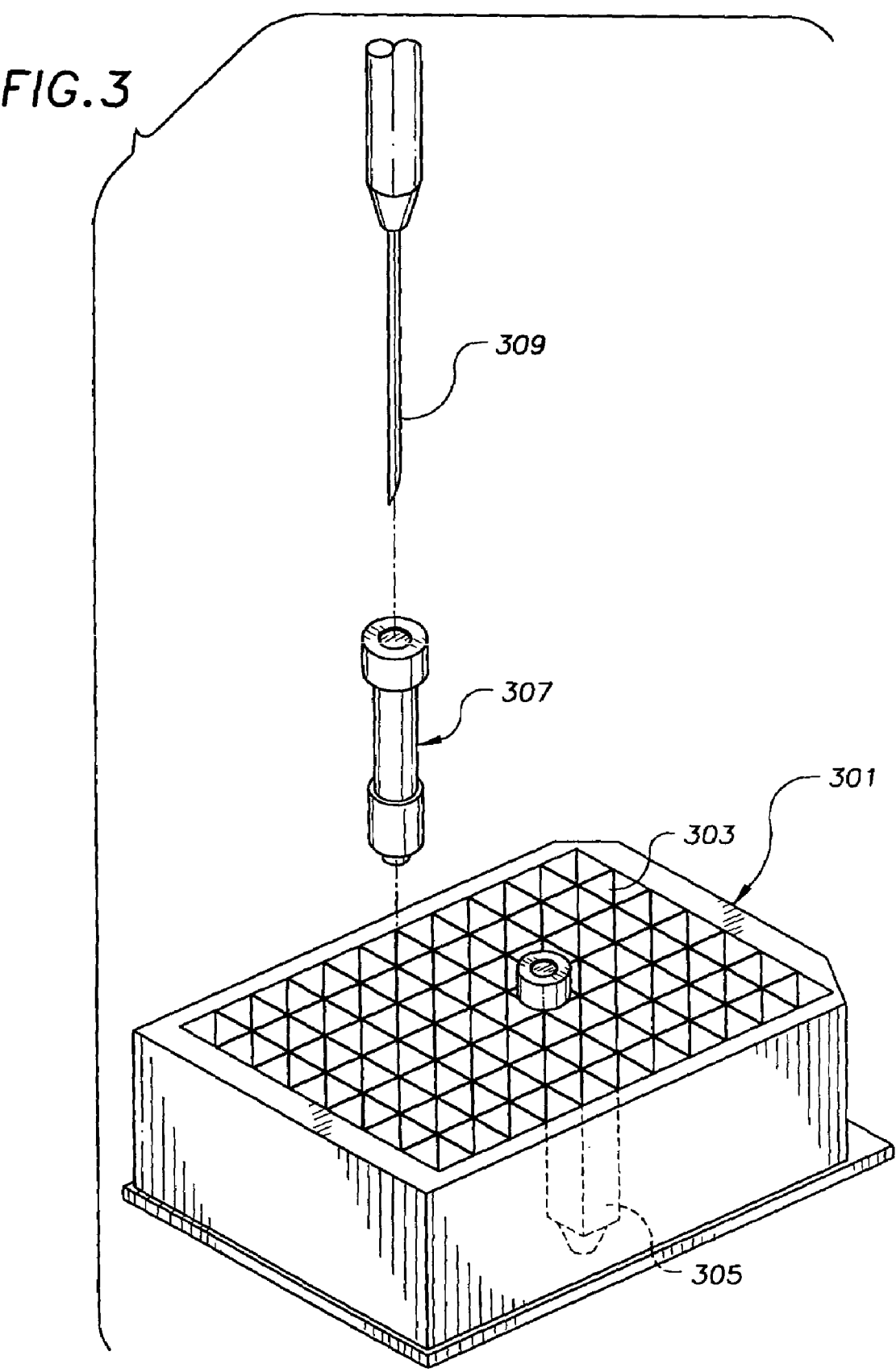

SAMPLE COLLECTION AND PROCESSING DEVICE

This is a continuation-in-part of U.S. application Ser. No. 09/620,331 filed Jul. 20, 2000, currently pending which is a continuation-in-part of U.S. application Ser. No. 09/263,229, filed Mar. 5, 1999, abandoned.

BACKGROUND OF THE INVENTION

The present invention relates to sample collection and processing devices and, more particularly, to sample processing and collection devices used with automated sampling and testing equipment.

The growth in medical and pharmaceutical research as well as diagnostic analysis and testing has created a need for equipment and procedures for low cost, high-speed sample collection and processing. Automated equipment is available for filling and retrieval of samples from sample wells, vials, bottles and other containers.

Microplates comprising a plurality of sample wells provide a convenient means to store samples. Automated equipment positions microplates for sample filling, retrieving, and analysis. Despite improvements in sample handling equipment, many applications require manual labor when performing evolutions such as; preparing sample containers or vials, relocating sample containers, and passing sample fluids through process elements such as absorbents, adsorbents, filters, solid phase extraction mediums, or additive compound materials. Manual processing steps are usually required when sample numbers are insufficient to justify design and building custom automated equipment.

Often the wells of microplates are used as the sample containers. In other applications, vials or sample bottles are inserted into the wells of microplates to contain the samples or testing fluids.

Certain types of testing such as chromatography, combinatorial chemistry, or high-throughput screening utilize processing of a sample by a processing element such as solid phase extraction medium, a filter, or an adsorbent disk. The compounds of interest are recovered by passing solvents through the processing element. This process requires multiple steps that are difficult to automate, especially if the sample numbers are not sufficiently large to justify specialized equipment, containers and processes.

OBJECTS AND SUMMARY OF THE INVENTION

Therefore, an object of the present invention is to provide a sample collection and processing device which is well suited to automation utilizing standard laboratory testing equipment, containers, and procedures.

Another object of the present invention is to provide a sample collection and processing device which utilizes a penetrating sample extraction/depositing element such as a hypodermic needle to insert, remove or reposition the sample collection and processing device into, or out of, sample containers without special connection or attachment devices.

Another object of the present invention is to provide a sample collection and processing device which incorporates integral process elements such as filters, adsorbent or absorbent disks, solid phase extraction mediums and additive compound materials.

Another object of the present invention is to provide a sample collection and processing device which allows sample collection and extraction of a sample without removal of the device from the sample container.

Another object of the present invention is to provide a sample collection and processing device which is low in cost.

Still another object of the present invention is to provide a sample collection and processing device which is compatible with many different sample containers or sample blocks.

Yet another object of the present invention is to provide a volume-adjusting insert for sample vessels or wells which reduces the volume of the sample vessel or well, allows communication of sample fluid into and out of the insert, and allows positioning of the insert with a penetrating sample element.

The sample collection and processing device comprises a body insertable into a sample container such as a sample vessel, or the well of a sample block or tray. The device has a septum at the top end of the body, an elongated sample chamber interior to the body and, optionally, a sample collection and deposit opening at the bottom end of the body. The optional septum is penetrable by a penetrating fluid sample deposit/extraction element such as a hypodermic needle. The device may be sized for a loose or tight fit in a sample bottle, vial, sample block well, or other form of sample container. The septum seals the hypodermic needle to the elongated sample chamber of the sample device.

The elongated sample chamber provides axial alignment of the device with the needle when the needle is inserted into the sample chamber. The combination of frictional engagement of the hypodermic needle with the septum and/or the elongated chamber and alignment of the needle and the sample chamber allows accurate positioning of the sample collection and processing device relative to other equipment or devices by the hypodermic needle. No special clamping or extra positioning equipment is required for withdrawal, moving and insertion of the sample device into, and out of, a sample container. Alternatively, an entire sample container may be moved by the hypodermic needle when the sample collecting and processing device is sized for a tight fit with the sample container.

The sample chamber is open to, and communicates with, the sample collection and deposit opening at the bottom end of the device. Optionally, the device comprises one or more sample processing elements such as adsorbent or absorbent disks, filters, solid phase extraction elements, or compound additive elements located in a process chamber positioned between the sample chamber and the sample collection and deposit opening. The device permits sample or processing fluid flow from the hypodermic needle to the bottom opening, or alternatively, between the opening and the hypodermic needle.

Other embodiments of the sample device incorporate a needle guide between the top septum and the sample chamber. The needle guide positions the needle as it exits the septum to guide the needle into the sample chamber. In still other embodiments, a second septum or penetrable seal is positioned at the bottom end of the elongated sample chamber. The penetrable seal allows the hypodermic needle to fully penetrate the sample device and deposit or extract sample in a container at a level below the device without removing the sample device from the container.

One embodiment of the invention comprises a volume-adjusting sealed insert for a sample well or vessel. The insert has a body with a through-chamber and a septum seal at the top of the insert. A seal surface on the outside of the body seals against the inside surface of the sample vessel to define a reduced-volume sample chamber comprising the through-chamber of the body and a lower chamber formed between the bottom of the sealed insert and the bottom of the sample vessel. Sample fluid injected into the insert from a penetrating sample element can be directed to and from the through-chamber and the lower chamber.

In bottom-extraction sample vessels, the sample fluid also communicates with the bottom extraction sample opening. The insert with septum and through-chamber sealed in the vessel allows the penetrating sample element such as a hypodermic needle to provide the hydraulic pressure to transport the sample through the insert, through a processing element (such as an absorbent disc) and exit through the bottom-extraction opening of the vessel.

Such an insert provides volume adjustment of a sample well in several ways. The insert may be used as a volume-reducing insert in which the reduced volume of the through-chamber and/or lower chamber provides an effective micro-sampling vessel. The insert may also be used to provide an enhanced-volume capability in that a needle of a syringe inserted into the septum and through-chamber provides a selectably large sample volume which may be passed through a processing element below the insert. Thus, the insert of the present invention provides a means to increase the flexibility of existing sample wells for many sampling purposes.

One embodiment of the sample device utilizes an integral drip tube at the bottom of the device. The drip tube has an opening at the bottom of a conical portion which allows the sample device to be partially submerged in a sample fluid and fluid withdrawn by a hypodermic needled inserted into the top septum of the device. The sample fluid may be processed by processing elements such as filters or frits in the bottom portion of the device and then transported in the device to another processing location or stored. Alternatively, a sample fluid may be inserted into the sample device by the hypodermic needle and the sample processed by the processing elements and discharged into a container or vessel.

BRIEF DESCRIPTION OF THE DRAWINGS

These and other features, aspects and advantages of the present invention will become better understood with regard to the following description, appended claims and accompanying drawings where:

FIG. 2A is a side elevation and partial cross-section drawing of embodiment 200 of the sample collection and processing device held by a hypodermic needle, the device being inserted into a sample well;

FIG. 2B is a side elevation and partial cross-section drawing of embodiment 200 of the sample collection and processing device inserted into a sample well and a vacuum drawn in the device by the hypodermic needle, drawing a sample fluid into the device through a processing element;

FIG. 2C is a side elevation and partial cross-section drawing of embodiment 200 of the sample collection and processing device inserted into a second sample well by the hypodermic needle, the needle injecting a solvent into the sample chamber and through the processing element into the second sample well;

FIG. 2D is a side elevation and partial cross-section drawing of embodiment 200 of the sample collection and processing device inserted into the second sample well and the needle further inserted into the sample device so that the needle fully penetrates a bottom penetrable seal so that the needle can extract sample in the second sample well below the device without removal of the sample device;

FIG. 3 is a perspective drawing of an embodiment of the sample collection and processing device insertable into one of the wells of a 96 well sample block by a hypodermic needle;

DESCRIPTION OF THE PREFERRED EMBODIMENTS

The following is a description of the preferred embodiments of a sample collection and processing device suitable for high speed automated sampling machinery.

Figure 1:
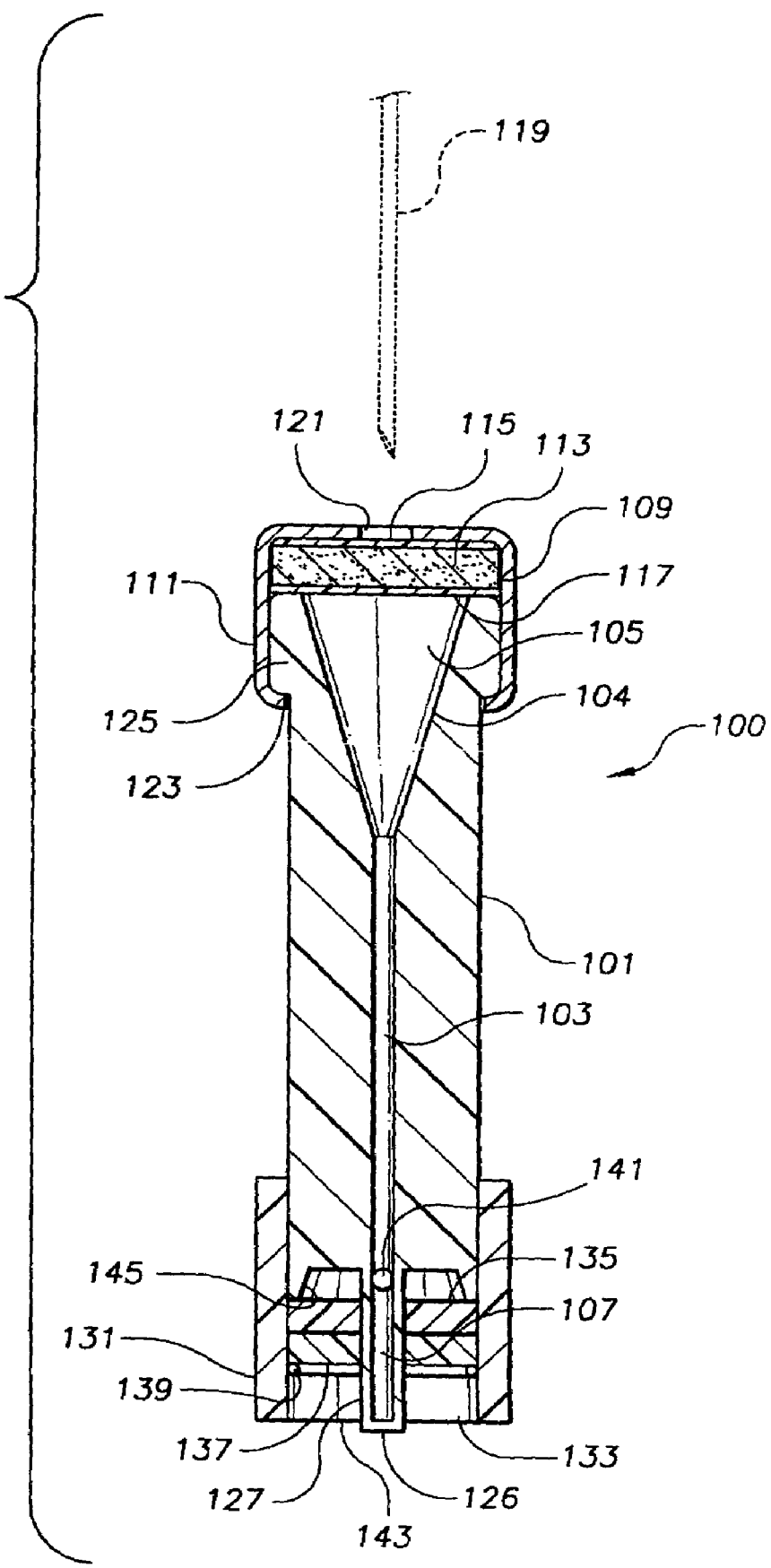
FIG. 1 is a cross-section drawing of embodiment 100 of the sample collection and processing device having a crimp cap with integral septum, and a bottom penetrable seal, the septum and the bottom seal penetrable by a hypodermic needle shown in phantom lines.

FIG. 1 is an elevation drawing of embodiment 100 of the sample collection and processing device. Body 101 defines an interior sample chamber 103 having a first or top end 105 and a second or bottom end 107. In the preferred embodiment, body 101 made of a chemically inert plastic material such as PTFE or polypropylene. Body 101 may be injection molded, die cast, machined, or made by other forming techniques. In still other embodiments, body 101 may be made of glass, metal, ceramics or composites. Septum 109 in end cap 111 encloses end 105 of chamber 103. Septum 109 comprises a sealant 113 such as silica gel sandwiched between upper seal layer 115 and lower seal layer 117. Seal layers 115 and 117 are made of a chemically inert material such as PTFE.

Septum 109 maintains sealing of chamber 103 during, and subsequent to, penetration of a deposit/extraction element such as hypodermic needle 119. Opening 121 in end cap 111 facilitates penetration of needle 119 into chamber 103. Crimp edge 123 of end cap 111 secures end cap 111 to flange 125 of body 101. In the preferred embodiment, end cap 111 is a metal crimp cap such as aluminum. In other embodiments, end cap 111 may be made of plastic, glass or composites. In still other embodiments, end cap 111 may be a snap cap.

In the preferred embodiment, bottom end 107 of sample chamber 103 comprises reduced-diameter lower body portion 127. Penetrable seal 126, located at the bottom end 107 seals the bottom end of sample chamber 103. In the preferred embodiment, seal 126 is a non-through portion of sample chamber 103 formed during injection molding and made of the same material as body 101. In other embodiments, seal 126 is a separate seal made of a penetrable or deformable material such as plastic. In still other embodiments, seal 126 may be a septum similar to septum 109.

Lower portion 127 and end tube 131 define annular processing chamber 133. End tube 131 is attached to body 101 by interference fit, shrink fit, or adhesives. In other embodiments, end tube 131 is integrally molded with body 101. The preferred material for end tube 131 is PTFE. Upper processing element 135 and lower processing element 137 are retained in annular space 133 by an interference fit. Retention ring 139 improves retention of processing elements 135 and 137 in annular space 133. Processing elements 135 and 137 may be separation mediums such as absorbent or adsorbent disks, filters, or solid phase extraction mediums. In other embodiments, processing elements 135 and 137 may be additive media such as dissolvable additives.

Aperture 141 in lower portion 127 of body 101 allows communication of sample fluid in chamber 103 with annular processing space 133. In the preferred embodiment, aperture 141 is a drilled hole. Aperture 141 is drilled prior to attachment of end tube 131. In the preferred embodiment, processing elements 135 and 137 are positioned between aperture 141 and end opening 143. Lip 145 spaces elements 135 and 137 from aperture 141 and prevents blockage of aperture 141. Lip 145 also defines an upper portion of annular processing space 133 which provides a distribution area for fluid passing through processing elements 135 and 137.

The features of the device allow multiple useful functions, depending on the requirements. For example, the device processes sample fluids extracted by hypodermic needle 119. Needle 119 is inserted through septum 109 and into sample chamber 103. Conical section or guide 104 of chamber 103 acts as a needle guide to ensure the hypodermic needle is guided into the restricted diameter portion of chamber 103. In this embodiment, restriction of the diameter of chamber 103 is desirable to reduce the amount of sample retained inside the device. The restricted diameter portion of elongated sample chamber 103 also provides axial alignment of the device with needle 119.

A vacuum source (not shown) connected to hypodermic needle 119, draws a vacuum in chamber 103. Sample fluid, surrounding the lower portion of body 101, is drawn into chamber 103 and hypodermic needle 119 through bottom opening 143, passing through processing elements 137 and 135, and aperture 141. Processing elements 135 and 137 are selected to remove or pass desired components or contaminants of the sample fluid.

Sample components, removed by processing elements 135 and 137 are recovered by injecting solvent into chamber 103 by hypodermic needle 119. The positive pressure resulting from the injection of solvent into the chamber drives the solvent through aperture 141, through processing elements 135 and 137, and out bottom opening 143. The solvent, containing components washed or dissolved from elements 135 and 137 by the solvent may be extracted by hypodermic needle 119 simply by further inserting hypodermic needle through penetrable seal 126 and connecting a vacuum source to needle 119. The sample and solvent processes may also be reversed. For example, hypodermic needle 119 may inject a sample into chamber 103, through aperture 141, elements 135 and 137, and out bottom opening 143. Processing elements 135 and 137 retain desired components of the sample. Placement of the device in a solvent and connection of a vacuum source to needle 119 allows collection of the solvent containing the desired components after passing through elements 135 and 137. In still other embodiments, processing elements 135 and 137 may be used to mix additives contained in the elements to a sample or solvent processed by the device.

FIGS. 2A–2D show embodiment 200 of the sample collection and processing device and its use in a sample well. Sample processing device 200 comprises tubular body 201 defining outer sample chamber 203. Needle guide 205 guides needle 227 into inner sample tube 207 defining inner sample chamber 209. Upper penetrable seal or septum 211 seals the upper portion of inner sample chamber 209 and lower penetrable seal or septum 213 seals the lower end of inner sample chamber 209. Resilient edge 210 secures snap cap 212 onto tubular body 201. In the preferred embodiment, tubular body 201, needle guide 205 and inner sample tube 207 are made of a plastic material such as polypropylene. In other embodiments, these components are made of metal, glass or composites. In the preferred embodiment, snap cap 212 is made of a resilient plastic material such as polyethylene or polypropylene.

Aperture 215 allows communication between inner chamber 209 and outer sample chamber 203. A processing element 216, made up of a processing material 218 sandwiched by upper frit 217 and lower frit 219, is positioned in the lower portion of outer sample chamber 203, between aperture 215 and outer sample chamber 203 bottom end opening 221. Frits 217 and 219 retain processing material 218 but allow sample fluids and solvents to pass through. Processing material 218 may be an adsorbent material, a solid phase extraction media, a filter, or an additive material.

FIG. 2A shows sample collection and processing device 200 being inserted in sample well 223 containing sample 225. Hypodermic needle 227 has been partially inserted into inner chamber 209 and retained in needle 227 by frictional forces with septum 211 and, in some embodiments, by frictional forces with inner sample tube 207. Support element 229, part of the external sampling equipment, supports needle 227 and holds sample device 200 during withdrawal of needle 227.

FIG. 2B shows device 200 inserted into sample well 223 until lower cap edge 239 of FIG. 2A contacts sample well top 241 by lowering hypodermic needle 227 in direction 243. A vacuum in hypodermic needle 227 draws sample 225 through processing element 216 and into outer sample chamber 203. Sample 225 is also drawn into inner sample chamber 209 through aperture 215. Sample device 200 containing the processed sample 225 is withdrawn by raising hypodermic needle 227 in direction 245.

FIG. 2C shows sample device 200 inserted in a second sample well 247 utilizing hypodermic needle 227. The sample well may be empty when device 200 is inserted. Solvent 228, injected by hypodermic needle 227 into inner sample chamber 209, passes through aperture 215, into outer sample chamber 203, and dissolves sample contaminants or components retained in processing element 216. The processed solvent 249, containing the dissolved contaminants, passes through end opening 221 and collects in the bottom of sample well 247.

FIG. 2D shows hypodermic needle 227 fully inserted through device 200 in the direction of arrow 246 so that hole 251 in the end of hypodermic needle 227 penetrates penetrable seal 213. Attaching a vacuum source to hypodermic needle 227 allows extraction of processed solvent 249 without removal of device 200 from well 247. The same hypodermic needle is used for sample device insertion into the sample well, extraction of the sample through a processing element to process the sample and retain sample contaminants, movement of the sample device to a second empty sample well, injection of solvents through the processing element to dissolve contaminants retained in the processing elements, and extraction of the processed solvent containing the dissolved contaminants.

FIG. 3 shows a perspective view of sample block 301 comprising a matrix of 12 rows of sample wells 303. Each row containing 8 wells. Sample wells 303 may comprise rectangular side walls 305, or cylindrical walls. Sample collection and storage devices 307 are inserted manually, or retained by hypodermic needles 309 and inserted or removed individually or in groups. Use of sample block 301 with sample device 307 allows processing of 96 samples quickly and reliably by automated equipment. In the preferred embodiment, sample block 301 is made of a plastic material such as polypropylene. In other embodiments, sample block 301 is made of glass, metal, composites or ceramics.

Other sample blocks having different numbers, arrays and sizes of wells may be used with the sample processing devices. Individual sample containers may also be used with the devices. Other fluids such as air or sample gasses may be sampled and processed with the device.

Figure 4:
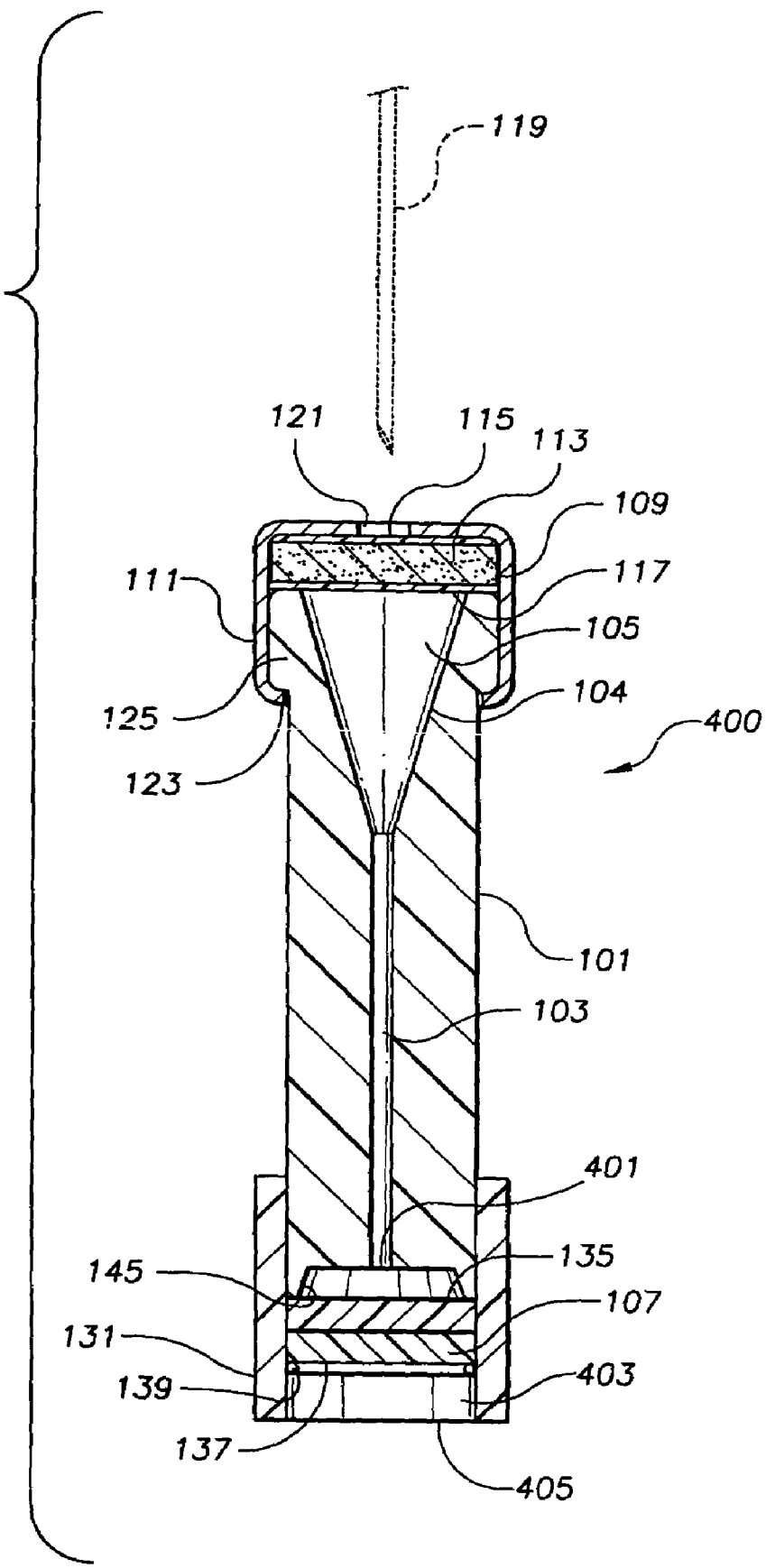
FIG. 4 is a cross-section of embodiment 400 of the sample collection and processing device moveable by a hypodermic needle.

FIG. 4 shows embodiment 400 of the sample collection and processing device. In this embodiment, septum 109 seals hypodermic needle 119 with chamber 103 when hypodermic needle 119 is inserted into the device similar to that shown in FIG. 2A. Sealing of hypodermic needle 119 allows device 400 to collect a sample through the bottom opening 405 of the device when a vacuum is drawn in needle 119. Sample drawn into opening 405 passes through processing elements 137 and 135 before entering chamber 103 and needle 119. Sample or solvent may be injected by needle 119. Due to the sealing effect of septum 109, the injected sample passes into chamber 401 above sample processing elements 135 and 137, through processing elements 135 and 137, and out end 405.

Septum 109 also provides a means to attach device 400 to needle 119 by frictional contact with septum 109. The frictional contact allows needle 119 to remove and reposition device 400 by movement of needle 119. Additional frictional contact of needle 119 with the inside surface of chamber 103 provides an additional means to secure the device to needle 119. Needle guide 104 guides needle 119 into chamber 103.

Chamber 103 provides an alignment means for device 400 to ensure chamber 103 of sample device 400 remains aligned axially with needle 119 during movement or repositioning of the sample device. Maintenance of a close fit between chamber 103 inner diameter and needle 119 outer diameter provides the desired axial alignment. The diametrical clearance required to provide alignment may vary from a close sliding fit to a diametrical clearance of up to 0.20". In applications requiring close axial alignment, the diametrical clearance between needle 119 outer diameter and chamber 103 inner diameter is preferable less than 0.10", more preferably less than 0.05", and in the most critical applications, a diametrical fit of less than 0.002". In still other embodiments, a slight interference fit is employed.

The length of the reduced diameter portion (below needle guide 104) of chamber 103 should be sufficient to permit penetration of needle 119 to a depth providing good axial alignment of needle 119 to chamber 103 when subjected to external forces encountered during sampling procedures. In one embodiment, the reduced diameter portion of chamber 103 is at least two chamber diameters in length, and more preferably, at least five chamber diameters in length. In the most preferred embodiments, the reduced diameter portion of chamber 103 is at least 10 inner diameters in length.

Use of small diametrical clearances and reduction of chamber 103 and needle guide length reduces internal volume of the device. Internal volume reduction in some applications is desirable to reduce vacuum requirements and undesirable mixing of sample and solvent fluids. The external dimensions of the device may be chosen to fit any of a variety of sample containers or sample blocks. In alternative embodiments of the device, the processing chamber 403, processing elements 135 and 137, and optionally, end tube 131 are omitted. In these embodiments, the device is used as a sample collection and depositing device positionable by needle 119.

Figure 5:
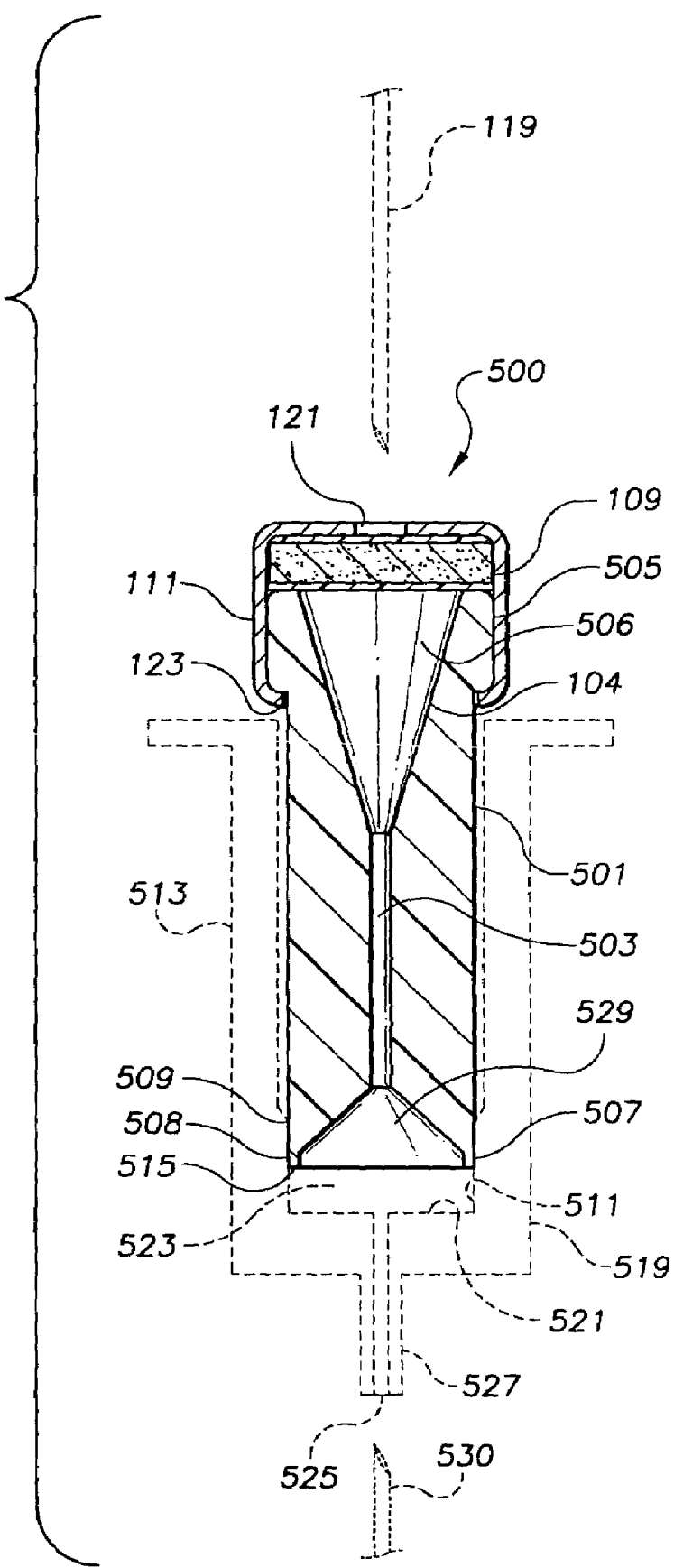
FIG. 5 is a cross-section of a volume-adjusting insert for a sample vessel comprising an insert body with a through-chamber, a crimp cap comprising a septum seal, and a seal surface on the lower portion of the insert body outside surface to seal the insert against the inside diameter of the sample vessel.

FIG. 5 is an elevation cross section of yet another embodiment of the invention incorporating a volume-adjusting insert 500 for bottom extraction sample wells and vessels. Insert 500 comprises a body 501 having a seal or septum 109 at the upper end 505 or needle guide 506 portion of sample chamber 503. A vessel seal surface 507 is disposed on the lower end portion 509 of body 501.

In the preferred embodiments, septum 109 is incorporated into a cap such as crimp cap 111. In other embodiments, septum 109 is incorporated into snap caps such as those disclosed in application Ser. No. 09/108,339, hereby incorporated as a reference. Or, septum 109 may be incorporated into screw caps such as open-hole or septum-penetrable screw caps. In still other embodiments, septum 109 is integral to body 501 at the upper portion of chamber 503 by inserting or forming a seal or septum material in the upper portion of the chamber.

In the preferred embodiments, seal surface 507 is an outside surface of seal ring 508 at the lower end portion 509 of body 501, sealing body 501 and a interior wall surface 511 of a bottom extraction sample vessel 513.

Other preferred embodiments comprise a bottom seal surface 515 of lower end portion 509. Bottom seal surface 515 may seal body 501 of insert 500 to a frit or processing element (similar to 135 of FIG. 1) in the lower portion 519 of sample vessel 513. Alternatively, bottom seal surface 515 may seal body 501 to bottom surface 521 of sample vessel 513 if no processing element is utilized.

Seal surfaces 507 and 515 seal body 501 to the lower end portion of vessel 513 to form a sealed vessel chamber 523 which communicates with chamber 503 of body 501 and bottom extraction opening 525 of bottom extraction tube 527. Bottom opening 525 may optionally be sealed by a septum or other seal means. Chamber 523 and 503 together define a reduced-volume sample chamber with a volume significantly reduced as compared to the volume of sample well 513. In some embodiments, body 501 is sufficiently long so that the effective volume of the sample chamber is the volume of chamber 503 only.

Sample fluid may be drawn into or expelled from extraction tube 527, for example by external suction or pressure chambers. Or, a penetration element 530 may be used to extract or deposit sample fluid from/into opening 525. Distributor chamber 529 at the lower portion of chamber 503 provides an expansion chamber for sample fluid from chamber 503 to vessel chamber 523.

In the preferred embodiments, body 501 is generally cylindrical in shape and made from a chemically inert plastic such as polypropylene or fluoropolymers, for example by injection molding. In other embodiments, body 501 is made from other polymers, glass, ceramics or metal. The shape and dimensioning of seal ring 508 is made to match and, seal against, the inner wall surface 511 at the depth of contact. In the preferred embodiments, seal surface 507 is a smooth surface dimensioned to provide a tight or slight interference fit with interior wall surface 511. The fit between body 501 and the interior wall surface of vessel 513 may be a loose fit above seal ring 508. In other embodiments, the substantial portion of body 501 forms a seal or tight fit with the interior wall of vessel 513.

Figure 6:
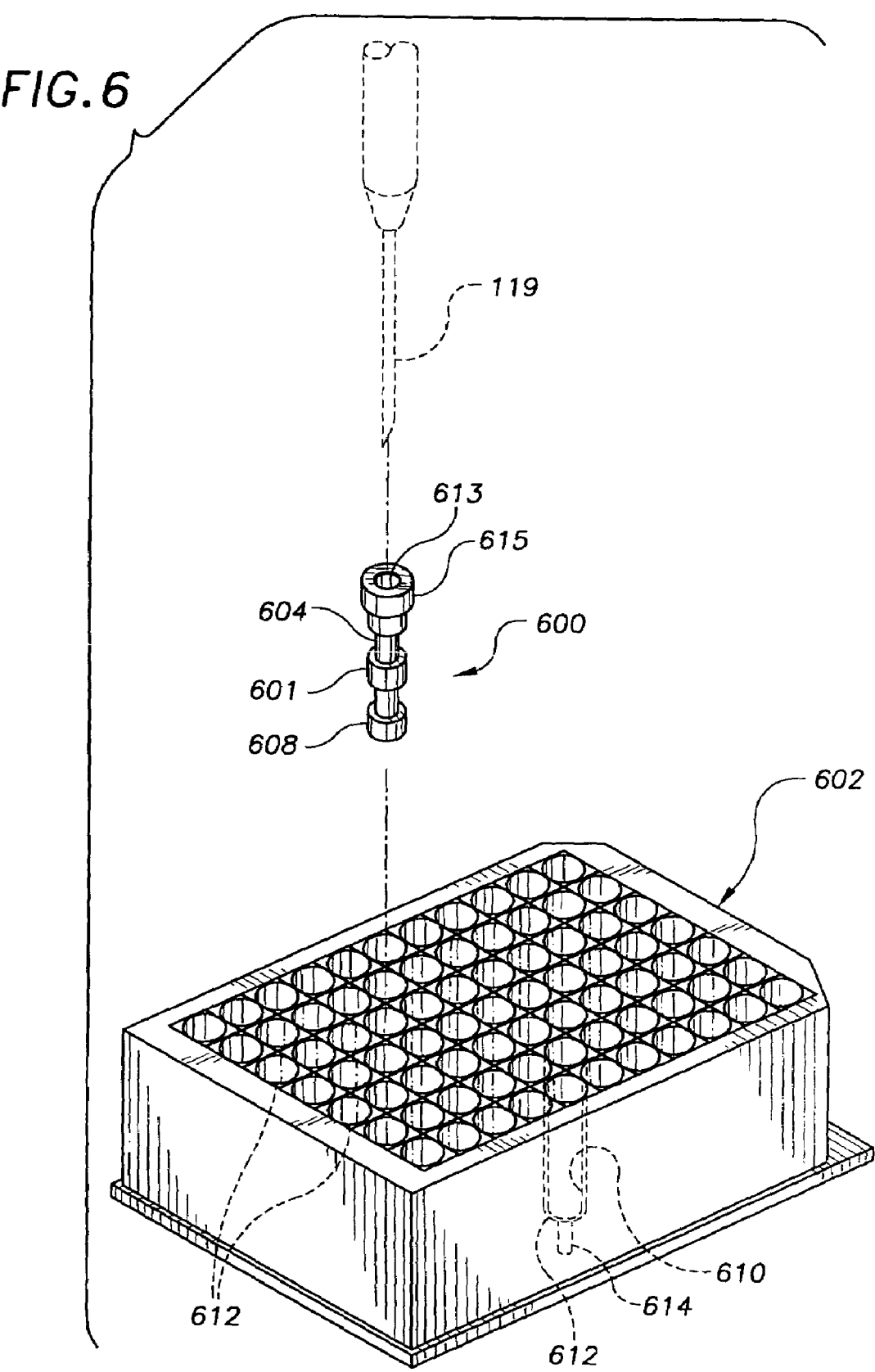
FIG. 6 is a perspective drawing of a volume-adjusting insert for a bottom-extraction sample block comprising multiple bottom-extraction sample wells, the insert insertable in the wells of the block.

FIG. 6 is an assembly drawing of a volume-adjusting insert 600 being inserted into a 96 well bottom-extraction tray 602. Body 601 of insert 600 is generally cylindrically shaped and may comprise void or recessed areas 604 providing lightness and material reduction. Seal ring surface 608 seals against interior wall surface 610 of sample well 612. Seal ring surface 608 may be a raised or larger diameter portion of body 601, or it may seat on a restricted diameter portion of sample well 612. Septum 613 of snap cap 615 provides a means for penetration device 119 to inject or extract sample fluid from insert 600 and sample wells 612 and to provide a means to withdraw, insert and move insert 600 as described previously. The septum seal material of the preferred embodiments is of sufficient resiliency to provide sufficient frictional engagement with the penetration device to allow positioning of the insert by the penetration device. Insert 600 comprises a through-sample chamber similar to chamber 503 of insert 500 of FIG. 5. Bottom extraction tube 614 also provides a means to inject and extract sample fluid from sample well 612. Although only one well 612 is shown in detail, other wells are similar. In a preferred embodiment, tray 602 is a 96 well sample tray configured in an 8×12 array.

Figure 7:
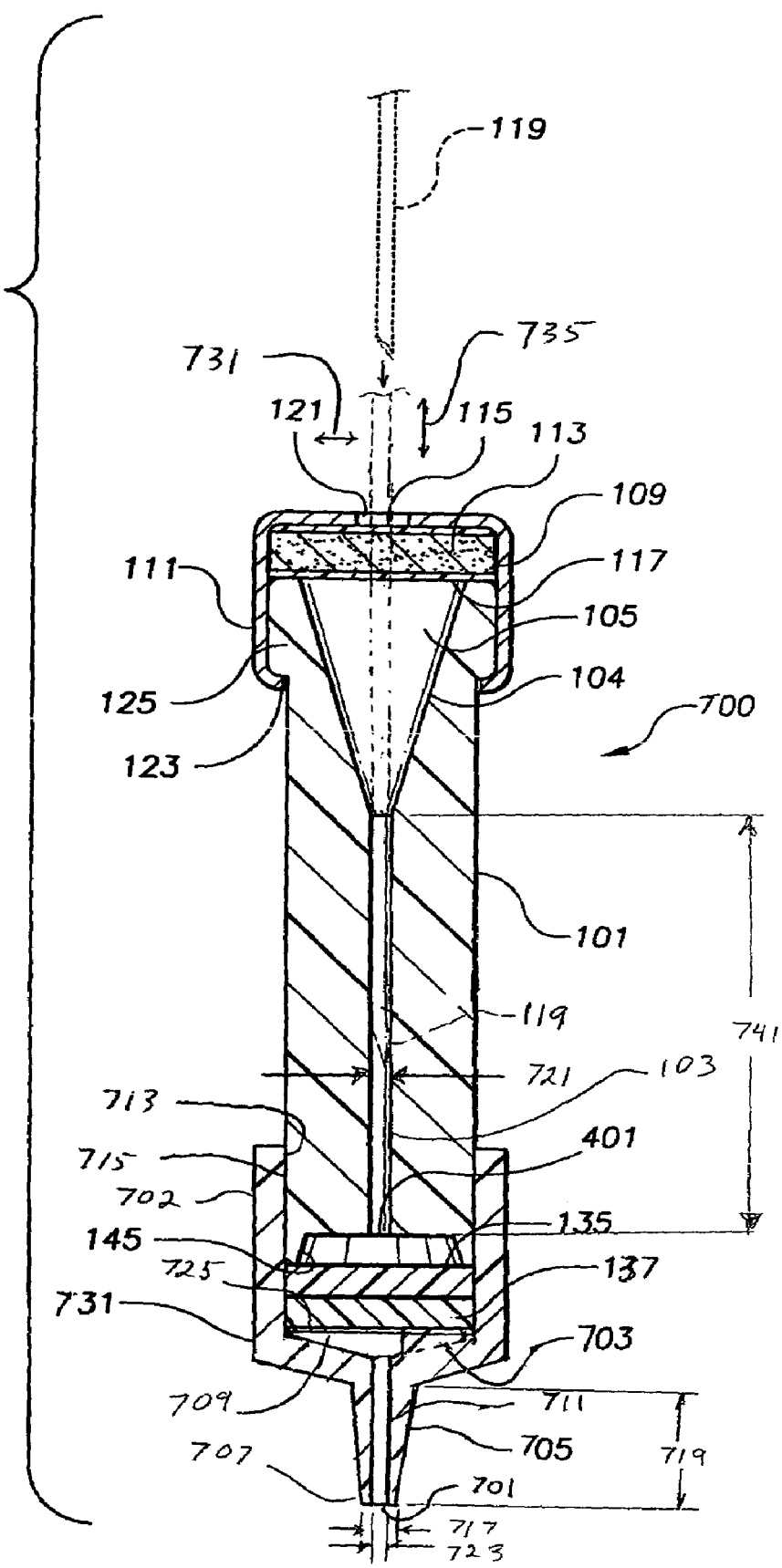
FIG. 7 is an elevation cross section drawing of an alternative embodiment of the sample processing device having a drip tube and opening at the bottom of the device.

FIG. 7 is an elevation cross section drawing of embodiment 700 of the sample collection and processing device similar to that of FIGS. 4 and 5 except that drip tube portion 731 is substituted for end tube 131 (embodiment 400) or vessel 513 (embodiment 500). Drip tube portion 731 connects to the bottom end of body 101 and defines an attachment portion 702, processing chamber 709, a converging nozzle 705 with nozzle chamber 711, and a bottom opening 701. Ribs 703 (one shown in cross section) of drip tube portion 731 retain and support optional processing elements such as filters or frits 135, 137 and may form a cruciform or star pattern in a plan view of drip tube 731.

Bottom opening 701 allows sample intake and discharge for device 700 from a sample container, vessel or well such as well 612 of tray 602 of FIG. 6. In the preferred embodiments, bottom opening 701 is open and provides fluid communication from bottom opening 701 to septum 109 through nozzle chamber 711, processing chamber 709, optional processing elements 135 and 137, expansion chamber 401, reduced-diameter chamber 103, conical guide 104 and needle 119 when inserted into septum 109. Fluid can be deposited by needle 119 through the device and out of bottom opening 701 or, alternatively, withdrawn by suction by needle 119 when nozzle 705 is inserted in a fluid. Needle 119 is typically part of a syringe and hollow needle assembly known in the art, but can be any type of penetrating sample deposit/extraction element capable of injecting or withdrawing fluid from device 700.

In the preferred embodiments, drip tube portion 731 is incorporated in an end cap made of the same material as body 101 and permanently attached by an interference fit, welding or adhesives after installation of optional processing elements 135, 137. In still other embodiments, drip tube 731 is a removable end cap and utilizes seal surface 713 of drip tube 731 and seal surface 715 of body 101 to prevent fluid leakage between the components. The end cap may be made removable by a tight fit, snap fitting, or other releasable fittings known in the art. Still other embodiments utilize a sealed septum at end 707 of drip tube 731 similar to penetrable seal 126 of FIG. 1. Still other embodiments utilize septum snap caps at end 105 of the device instead of septum crimp caps.

The small diameter of end 707 of nozzle 705 minimizes wetted area and dripping during sampling evolutions. In the preferred embodiments, diameter 717 of nozzle 705 is chosen to be of a diameter small enough to result in accumulation of a single drop of fluid when the nozzle is inserted and removed from a sample liquid. In the preferred embodiments, diameter 717 of nozzle 105 is less than one-quarter inch. In the more referred embodiments, diameter 717 is less than one-eight inch. In the preferred embodiments, nozzle 705 is conical in shape and the length 719 of nozzle 705 is greater than one-eight inch to allow insertion in a sample without wetting the body of the device. In the more preferred embodiments, length 719 is greater than one-fourth inch. Length 719 is preferably at least two, and more preferably, at least four times the diameter 723 of bottom opening 701.

The construction features of septum 109, conical guide 104, and chamber 103 are similar to those of FIGS. 4 and 5 and permit the device to be positioned or relocated to sample locations spaced horizontally 731 and vertically 735 by needle 119 when needle 119 is inserted into chamber 103. The selected dimensions of conical guide 104 and chamber 103 provide the alignment means necessary for accurate positioning of the device by needle 119. The frictional engagement with septum 109, optional seals 115 and 117 and, in some embodiments engagement with chamber 103, provide the attachment means for positioning device 700 with needle 119.

In order to provide the desired needle alignment features and low sample volume, the diameter 721 of reduced-diameter chamber 103 and diameter 723 of nozzle chamber 711 are selected to be small in comparison to the diameter 725 of processing chamber 709. In the preferred embodiments, diameters 721 and 723 are less than one half of diameter 725. In the more preferred embodiments, diameters 721 and 723 are less than one fourth of diameter 725. In the still more preferred embodiments, diameters 721 and 723 are less than one eighth of diameter 725. A length-to-diameter ratio of reduced-diameter chamber 103 (length 741/diameter 721) of greater than 4, or more preferable greater than 8 provides improved axial alignment of device 700 to needle 119.

Other embodiments may employ different shape sample processing devices and sample wells, having rectangular, triangular or other shaped cross sections. Devices may be used with single or multi-well sample wells or vessels designed for bottom sample extraction known in the art.

Accordingly, the reader will see that the SAMPLE COLLECTION AND PROCESSING DEVICE provides a device which collects and processes a sample in conjunction with a sample and extraction element such as a hypodermic needle. The device provides the following additional advantages:

The sample device collects or deposits sample fluids or solvents into or from a wide variety of sample containers;

The hypodermic needle becomes the conveyance means for inserting the sample device in a container, sample vial or sample block well, removing the device from the container, and moving the device to another container or processing location;

The device accepts a variety of processing elements such as solid phase extraction mediums, absorbents, adsorbents, filters and additive compounds;

The device simplifies automation of sampling processes;

The device allows the user to optimize the volume of the sample for the desired analytical method;

The device allows a hypodermic needle to provide the hydraulic pressure necessary to convey sample fluid through the device; and The device is simple and low in cost.

Although the description above contains many specifications, these should not be construed as limiting the scope of the invention but as merely providing illustrations of some of the presently preferred embodiments of this invention. For example, the sample processing device may be made as a single component including the septum. Or reduced-diameter chamber 103 may extend only partially through body 101 and additional chamber portions added. Thus the scope of the invention should be determined by the appended claims and their legal equivalents, rather than by the examples given.

I claim:

1. A sample processing device for liquid sample, intake and discharge from a sample vessel, the device comprising:
    a body comprising a top portion, a bottom portion and a reduced-diameter chamber;
    a septum disposed on said top portion of said body;
    a drip tube comprising a bottom opening and defining a bottom end of said bottom portion of said body, said bottom opening in fluid communication with said septum;
    a conical needle guide disposed between said septum and said reduced-diameter chamber; and
    a processing chamber disposed between said bottom opening and said reduced-diameter chamber;
    wherein a diameter of said reduced-diameter chamber and said bottom opening of said drip tube are less than one half of a diameter of said processing chamber and said drip tube extends downwardly from said body and converges inwardly from said processing chamber to define a drip tube nozzle of diameter sufficiently small for excessive sample to converge into a single drop on said nozzle when said nozzle is inserted and removed from a liquid sample in said sample vessel.

2. The sample processing device of claim 1 wherein said diameter of said reduced-diameter chamber and said bottom opening of said drip tube are less than one fourth of said diameter of said processing chamber.

3. The sample processing device of claim 1 wherein said diameter of said reduced-diameter chamber and said bottom opening of said drip tube are less than one eight of said diameter of said processing chamber.

4. The sample processing device of claim 1 wherein a length of said reduced-diameter chamber is greater than four times a diameter of said reduced-diameter chamber to define an axial alignment portion of said sample processing device with a penetrating sample deposit/extraction element inserted into the device.

5. The sample processing device of claim 1 wherein a length of said reduced-diameter chamber is greater than eight times a diameter of said reduced-diameter chamber to define an axial alignment portion of said sample processing device with a penetrating sample deposit/extraction element inserted into the device.

6. The sample processing device of claim 1 wherein said drip nozzle having a length of at least two times a diameter of said bottom opening.

7. The sample processing device of claim 1 wherein said drip nozzle having a length of at least four times a diameter of said bottom opening.

8. A method of testing samples, the method comprising the steps:
    inserting a penetrating sample deposit/extraction element into a sample processing device, said sample processing device comprising a top and a bottom opening of a drip tube defining an axial direction, a septum seal in an upper portion of the device, a reduced-diameter chamber disposed between said septum seal and said drip tube and communicating with said bottom opening of said device, and a processing chamber disposed between said bottom opening and said reduced-diameter chamber wherein said drip tube extends downwardly from said body and converges inwardly from said processing chamber to define a drip tube nozzle of diameter sufficiently small for excessive sample to converge into a single drop on said nozzle;
    transferring sample fluid between said penetrating sample deposit/extraction element and a first sample vessel via said device; and
    physically positioning said sample processing device to another sample processing location by movement of said penetrating sample deposit/extraction element.

9. The method of testing samples of claim 8 comprising the additional steps:
    transferring said sample fluid through a processing element disposed in said sample processing device during said step of transferring sample fluid between said penetrating sample deposit/extraction element and said device; and
    transferring said sample fluid between said penetrating sample deposit/extraction element and a second sample vessel after said step of physically positioning said sample processing device to another sample processing location by movement of said penetrating sample deposit/extraction element.

10. The sample processing device of claim 1 wherein said drip tube comprises an end cap engaged to said bottom portion of said body.

11. The sample processing device of claim 10 wherein said end cap comprises a support element for a processing element disposed in said processing chamber.

12. The sample processing device of claim 1 comprising a sample processing element disposed in said processing chamber.

13. A sample processing device for liquid sample intake and discharge from a sample vessel, the device comprising:
    a body comprising a top portion, a bottom portion and a reduced-diameter chamber;
    a septum disposed on said top portion of said body;
    a drip tube comprising a bottom opening and defining a bottom end of said bottom portion of said body, said bottom opening in fluid communication with said septum; and
    a processing chamber comprising a diameter greater than a diameter of said reduced-diameter chamber disposed between said drip tube and said reduced-diameter chamber;
    wherein said drip tube extends downwardly from said body and converges inwardly from said processing chamber to define a drip tube nozzle of diameter sufficiently small for excessive sample to converge into a single drop on said nozzle when said nozzle is inserted and removed from a liquid sample in said sample vessel.

14. The sample processing device of claim 13 wherein said drip tube nozzle is conical in shape and comprises an end diameter of less than one-eighth inch.

15. The sample processing device of claim 13 wherein said drip tube nozzle is conical in shape, extends at least one quarter inch in length and comprises an end diameter of less than one-eighth inch.

16. The sample processing device of claim 13 comprising a conical guide disposed between said septum and said reduced-diameter chamber.

17. The sample processing device of claim 14 wherein said reduced-diameter chamber comprises a length-to-diameter ratio of greater than 4 whereby said reduced-diameter chamber provides axial alignment of a penetrating sample deposit/extraction element inserted into said reduced-diameter chamber.

18. The sample processing device of claim 14 wherein said reduced-diameter chamber comprises a length-to-diameter ratio of greater than 8 whereby said reduced-diameter chamber provides axial alignment of a penetrating sample deposit/extraction element inserted into said reduced-diameter chamber.

* * * * *